(12) United States Patent
Hanina et al.

(10) Patent No.: US 10,149,648 B2
(45) Date of Patent: Dec. 11, 2018

(54) METHOD AND APPARATUS FOR MONITORING MEDICATION ADHERENCE

(71) Applicant: Ai Cure Technologies LLC, Mt. Kisco, NY (US)

(72) Inventors: Adam Hanina, New York, NY (US); Gordon Kessler, Mt. Kisco, NY (US); Lei Guan, Jersey City, NJ (US)

(73) Assignee: Ai Cure Technologies LLC, Mount Kisco, NY (US)

( * ) Notice: Subject to any disclaimer, the term of this patent is extended or adjusted under 35 U.S.C. 154(b) by 0 days.

(21) Appl. No.: 15/840,836

(22) Filed: Dec. 13, 2017

(65) Prior Publication Data

US 2018/0296159 A1    Oct. 18, 2018

Related U.S. Application Data

(63) Continuation of application No. 15/337,551, filed on Oct. 28, 2016, now Pat. No. 9,844,337, which is a
(Continued)

(51) Int. Cl.
*H04N 9/47*     (2006.01)
*H04N 7/18*     (2006.01)
(Continued)

(52) U.S. Cl.
CPC .......... *A61B 5/4833* (2013.01); *A61B 5/004* (2013.01); *A61B 5/0077* (2013.01); *A61B 5/1114* (2013.01); *A61B 5/1123* (2013.01); *A61B 5/1128* (2013.01); *A61B 5/4205* (2013.01); *A61B 5/486* (2013.01); *A61B 5/742* (2013.01); *B01D 29/0093* (2013.01); *B01D 29/56* (2013.01); *B01D 39/06* (2013.01); *B01D 39/1623* (2013.01); *B01D 39/2017* (2013.01); *G06K 9/00335* (2013.01); *G06K 9/00355* (2013.01); *G06T 7/70* (2017.01); *H04N 5/23219* (2013.01); *H04N 5/23293* (2013.01);
(Continued)

(58) Field of Classification Search
None
See application file for complete search history.

(56) References Cited

U.S. PATENT DOCUMENTS 3,814,845 A    6/1974  Hurlbrink et al.
5,065,447 A   11/1991  Barnsley et al.
(Continued)

OTHER PUBLICATIONS

Ammouri, et al., "Face and Hands Detection and Tracking Applied to the Monitoring of Medication Intake," Computer and Robot Vision, 2008. CRV '08. Canadian Conference, 147(154):28-30, (May 2008).
(Continued)

*Primary Examiner* — Hung Q Dang
(74) *Attorney, Agent, or Firm* — Fish & Richardson P.C.

(57) ABSTRACT

A system and method for positioning a pill to be ingested by a user in a field of view of an image acquisition camera. The method includes the steps of determining a desired location of the mouth of a user in a field of view of an image acquisition camera, determining a current position of a pill to be ingested by the user in the field of view of the image acquisition apparatus, and indicating on a display a movement to be made by the user to move the pill towards mouth of the user.

15 Claims, 12 Drawing Sheets

Related U.S. Application Data continuation of application No. 14/073,525, filed on Nov. 6, 2013, now Pat. No. 9,486,720, which is a continuation of application No. 12/899,510, filed on Oct. 6, 2010, now Pat. No. 8,605,165.

(51) Int. Cl.

| | | |
|---|---|---|
| *H04N 5/77* | (2006.01) | |
| *H04N 5/775* | (2006.01) | |
| *A61B 5/00* | (2006.01) | |
| *G06T 7/70* | (2017.01) | |
| *A61B 5/11* | (2006.01) | |
| *B01D 39/16* | (2006.01) | |
| *B01D 39/20* | (2006.01) | |
| *G06K 9/00* | (2006.01) | |
| *H04N 5/232* | (2006.01) | |
| *B01D 39/06* | (2006.01) | |
| *B01D 29/56* | (2006.01) | |
| *B01D 29/00* | (2006.01) | |

(52) U.S. Cl.
CPC .. *B01D 2201/188* (2013.01); *B01D 2239/064* (2013.01); *B01D 2239/065* (2013.01); *B01D 2239/1233* (2013.01); *G06K 9/00912* (2013.01); *Y10T 428/249964* (2015.04); *Y10T 428/249969* (2015.04)

(56) References Cited

U.S. PATENT DOCUMENTS

| | | | |
|---|---|---|---|
| 5,441,047 A | 8/1995 | David et al. | |
| 5,544,649 A | 8/1996 | David et al. | |
| 5,619,991 A | 4/1997 | Sloane | |
| 5,646,912 A | 7/1997 | Cousin | |
| 5,752,621 A | 5/1998 | Passamante | |
| 5,764,296 A | 6/1998 | Shin | |
| 5,772,593 A | 6/1998 | Hakamata | |
| 5,810,747 A | 9/1998 | Brudny et al. | |
| 5,911,132 A | 6/1999 | Sloane | |
| 5,961,446 A | 10/1999 | Beller et al. | |
| 6,151,521 A | 11/2000 | Guo et al. | |
| 6,154,558 A | 11/2000 | Hsieh | |
| 6,233,428 B1 | 5/2001 | Fryer | |
| 6,283,761 B1 | 9/2001 | Joao | |
| 6,380,858 B1 | 4/2002 | Yarin et al. | |
| 6,409,661 B1 | 6/2002 | Murphy | |
| 6,421,650 B1 | 7/2002 | Goetz et al. | |
| 6,483,993 B1 | 11/2002 | Misumi et al. | |
| 6,484,144 B2 | 11/2002 | Martin et al. | |
| 6,535,637 B1 | 3/2003 | Wootton et al. | |
| 6,611,206 B2 | 8/2003 | Eshelman et al. | |
| 6,705,991 B2 | 3/2004 | Bardy | |
| 6,879,970 B2 | 4/2005 | Shiffman et al. | |
| 6,988,075 B1 | 1/2006 | Hacker | |
| 7,184,047 B1 | 2/2007 | Crampton | |
| 7,184,075 B2 | 2/2007 | Reiffel | |
| 7,256,708 B2 | 8/2007 | Rosenfeld et al. | |
| 7,277,752 B2 | 10/2007 | Matos | |
| 7,304,228 B2 | 12/2007 | Bryden et al. | |
| 7,307,543 B2 | 12/2007 | Rosenfeld et al. | |
| 7,317,967 B2 | 1/2008 | DiGianfilippo et al. | |
| 7,340,077 B2 | 3/2008 | Gokturk | |
| 7,395,214 B2 | 7/2008 | Shillingburg | |
| 7,415,447 B2 | 8/2008 | Shiffman et al. | |
| 7,448,544 B1 | 11/2008 | Louie et al. | |
| 7,562,121 B2 | 7/2009 | Berisford et al. | |
| 7,627,142 B2 | 12/2009 | Kurzweil et al. | |
| 7,657,443 B2 | 2/2010 | Crass et al. | |
| 7,692,625 B2 | 4/2010 | Morrison et al. | |
| 7,747,454 B2 | 6/2010 | Bartfeld et al. | |
| 7,761,311 B2 | 7/2010 | Clements et al. | |
| 7,769,465 B2 | 8/2010 | Matos | |
| 7,774,075 B2 | 8/2010 | Lin et al. | |
| 7,874,984 B2 | 1/2011 | Elsayed et al. | |
| 7,881,537 B2 | 2/2011 | Ma et al. | |
| 7,908,155 B2 | 3/2011 | Fuerst et al. | |
| 7,912,733 B2 | 3/2011 | Clements et al. | |
| 7,956,727 B2 | 6/2011 | Loncar | |
| 7,983,933 B2 | 7/2011 | Karkanias et al. | |
| 8,107,672 B2 | 1/2012 | Goto | |
| 8,321,284 B2 | 11/2012 | Clements et al. | |
| 2001/0049673 A1 | 12/2001 | Dulong et al. | |
| 2001/0056358 A1 | 12/2001 | Dulong et al. | |
| 2002/0026330 A1 | 2/2002 | Klein | |
| 2002/0093429 A1 | 7/2002 | Matsushita et al. | |
| 2002/0143563 A1 | 10/2002 | Hufford et al. | |
| 2003/0164172 A1 | 9/2003 | Chumas et al. | |
| 2003/0190076 A1 | 10/2003 | Delean | |
| 2003/0225325 A1 | 12/2003 | Kagermeier et al. | |
| 2004/0100572 A1 | 5/2004 | Kim | |
| 2004/0107116 A1 | 6/2004 | Brown | |
| 2004/0155780 A1 | 8/2004 | Rapchak | |
| 2005/0144150 A1 | 6/2005 | Ramamurthy et al. | |
| 2005/0148847 A1 | 7/2005 | Uchiyama | |
| 2005/0149361 A1 | 7/2005 | Saus et al. | |
| 2005/0180610 A1 | 8/2005 | Kato et al. | |
| 2005/0182664 A1 | 8/2005 | Abraham-Fuchs et al. | |
| 2005/0234381 A1 | 10/2005 | Niemetz et al. | |
| 2005/0267356 A1 | 12/2005 | Ramasubramanian et al. | |
| 2006/0066584 A1 | 3/2006 | Barkan | |
| 2006/0169294 A1* | 8/2006 | Kaler | A61B 5/073 128/899 |
| 2006/0218011 A1 | 9/2006 | Walker et al. | |
| 2006/0238549 A1 | 10/2006 | Marks | |
| 2007/0008112 A1 | 1/2007 | Covannon et al. | |
| 2007/0008113 A1 | 1/2007 | Spoonhower et al. | |
| 2007/0030363 A1 | 2/2007 | Cheatle et al. | |
| 2007/0041621 A1 | 2/2007 | Lin | |
| 2007/0118389 A1 | 5/2007 | Shipon | |
| 2007/0194034 A1 | 8/2007 | Vasiadis | |
| 2007/0233035 A1 | 10/2007 | Wehba et al. | |
| 2007/0233049 A1 | 10/2007 | Wehba et al. | |
| 2007/0233050 A1 | 10/2007 | Wehba et al. | |
| 2007/0233281 A1 | 10/2007 | Wehba et al. | |
| 2007/0233520 A1 | 10/2007 | Wehba et al. | |
| 2007/0233521 A1 | 10/2007 | Wehba et al. | |
| 2007/0265880 A1 | 11/2007 | Bartfeld et al. | |
| 2007/0273504 A1 | 11/2007 | Tran | |
| 2008/0000979 A1 | 1/2008 | Poisner | |
| 2008/0093447 A1 | 4/2008 | Johnson et al. | |
| 2008/0114226 A1 | 5/2008 | Music et al. | |
| 2008/0114490 A1 | 5/2008 | Jean-Pierre | |
| 2008/0138604 A1 | 6/2008 | Kenney et al. | |
| 2008/0140444 A1 | 6/2008 | Karkanias et al. | |
| 2008/0161660 A1 | 7/2008 | Arneson | |
| 2008/0162192 A1 | 7/2008 | Vonk et al. | |
| 2008/0178126 A1 | 7/2008 | Beeck et al. | |
| 2008/0201174 A1 | 8/2008 | Ramasubramanian et al. | |
| 2008/0219493 A1 | 9/2008 | Tadmor | |
| 2008/0239104 A1 | 10/2008 | Koh | |
| 2008/0273097 A1 | 11/2008 | Nagashima | |
| 2008/0275738 A1 | 11/2008 | Shillingburg | |
| 2008/0290168 A1 | 11/2008 | Sullivan et al. | |
| 2008/0297589 A1 | 12/2008 | Kurtz et al. | |
| 2008/0303638 A1 | 12/2008 | Nguyen et al. | |
| 2009/0012818 A1 | 1/2009 | Rodgers | |
| 2009/0018867 A1 | 1/2009 | Reiner | |
| 2009/0043610 A1 | 2/2009 | Nadas et al. | |
| 2009/0048871 A1 | 2/2009 | Skomra | |
| 2009/0095837 A1 | 4/2009 | Lindgren | |
| 2009/0127339 A1 | 5/2009 | Needhan et al. | |
| 2009/0128330 A1 | 5/2009 | Monroe | |
| 2009/0159714 A1 | 6/2009 | Coyne, III et al. | |
| 2009/0217194 A1 | 8/2009 | Martin et al. | |
| 2009/0245655 A1 | 10/2009 | Matsuzaka | |
| 2009/0259123 A1 | 10/2009 | Navab et al. | |
| 2009/0299142 A1 | 12/2009 | Uchiyama et al. | |
| 2010/0042430 A1 | 2/2010 | Bartfield | |
| 2010/0050134 A1 | 2/2010 | Clarkson | |
| 2010/0057646 A1 | 3/2010 | Martin et al. | |
| 2010/0092093 A1 | 4/2010 | Akatsuka et al. | |
| 2010/0130250 A1 | 5/2010 | Choi | |

(56) References Cited

U.S. PATENT DOCUMENTS

| | | | |
|---|---|---|---|
| 2010/0136509 | A1 | 6/2010 | Mejer et al. |
| 2010/0138154 | A1 | 6/2010 | Kon |
| 2010/0225773 | A1 | 9/2010 | Lee |
| 2010/0234792 | A1 | 9/2010 | Dacey, Jr. |
| 2010/0255598 | A1 | 10/2010 | Melker |
| 2010/0262436 | A1 | 10/2010 | Chen et al. |
| 2010/0316979 | A1 | 12/2010 | Von Bismarck |
| 2011/0004059 | A1 | 1/2011 | Arneson |
| 2011/0021952 | A1 | 1/2011 | Vallone |
| 2011/0069159 | A1 | 3/2011 | Soler et al. |
| 2011/0119073 | A1 | 5/2011 | Hanina et al. |
| 2011/0141009 | A1 | 6/2011 | Izumi |
| 2011/0153360 | A1 | 6/2011 | Hanina et al. |
| 2011/0161109 | A1 | 6/2011 | Pinsonneault et al. |
| 2011/0190595 | A1 | 8/2011 | Bennett et al. |
| 2011/0195520 | A1 | 8/2011 | Leider et al. |
| 2011/0275051 | A1 | 11/2011 | Hanina et al. |
| 2012/0046542 | A1 | 2/2012 | Csavoy et al. |
| 2012/0075464 | A1 | 3/2012 | Derenne et al. |

OTHER PUBLICATIONS

Batz, et al. "A computer Vision System for Monitoring Medication Intake," in Proc. IEEE 2nd Canadian Conf. on Computer and Robot Vision, Victoria, BC, Canada, 2005, pp. 362-369.

Bilodeau et al. Monitoring of Medication Intake Using a Camera System. Journal of Medical Systems 2011. [retrieved on Feb. 18, 2013] Retrieved from ProQuest Technology Collection.

Chen, Pauline W., "Texting as a Health Tool for Teenagers", The New York Times, Nov. 5, 2009, http://www.nytimes.com/2009/11/05/health/0512/899,510.

Danya International, Inc., "Pilot Study Using Cell Phones for Mobile Direct Observation Treatment to Monitor Medication Compliance of TB Patients", Mar. 20, 2009, www.danya.com/MDOT.asp.

Global Tuberculosis Control: A short update to the 2009 report, World Health Organization, (2009).

Huynh et al., "Real time detection, tracking and recognition of medication intake." World Academy of Science, Engineering and Technology 60 (2009), 280-287.

Mintchell, "Exploring the Limits of Machine Vision", Automating World, Oct. 1, 2011.

Osterberg, Lars and Blaschke, Terrence, "Adherence to Medication", New England Journal of Medicine 2005; 353:487-97, Aug. 4, 2005.

Super-Resolution, Wikipedia, (Oct. 5, 2010).

University of Texas, GuideView, Mar. 15, 2007, http://www.sahs.uth.tmc.edu/MSriram/GuideView.

Valin, et al. "Video Surveillance of Medication intake", Int. Conf. of the IEEE Engineering in Medicine and Biology Society, New York City, USA, Aug. 2006.

Wang et al. "Recent Developments in human motion analysis." Pattern Recognition 36 (220) 585-601 (Nov. 2001).

Whitecup, Morris S., "2008 Patient Adherence Update: New Approaches for Success", www.guideline.com, The Trend Report Series, (Oct. 1, 2008).

Final Office Action from PTO, (U.S. Appl. No. 12/620,686), (dated May 8, 2012), 1-24.

Final Office Action from PTO, (U.S. Appl. No. 13/558,377), dated May 7, 2013, 1-29.

Final Office Action from PTO, (U.S. Appl. No. 12/646,383), (dated May 8, 2012), 1-31.

Final Office Action from PTO, (U.S. Appl. No. 13/588,380), (dated Mar. 1, 2013), 1-27.

Final Office Action from PTO, (U.S. Appl. No. 12/646,603), (dated Feb. 1, 2012), 1-17.

Final Office Action from PTO, (U.S. Appl. No. 12/728,721), (dated Apr. 12, 2012), 1-31.

Final Office Action from PTO, (U.S. Appl. No. 12/815,037), (dated Sep. 13, 2012), 1-15.

Final Office Action from PTO, (U.S. Appl. No. 12/899,510), (dated Aug. 20, 2013).

Final Office Action from PTO, (U.S. Appl. No. 12/898,338), dated Nov. 9, 2012), 1-12.

Final Office Action from PTO, (U.S. Appl. No. 13/189,518), (dated Jul. 23, 2013), 1-16.

International Preliminary Report on Patentability, (PCT/US2010/056935) (dated May 31, 2012), 1-8.

Non-Final Office Action from PTO, (U.S. Appl. No. 12/620,686), (dated Dec. 21, 2011),1-78.

Non-Final Office Action from PTO, (U.S. Appl. No. 13/558,377), (dated Oct. 22, 2012), 1-21.

Non-Final Office Action from PTO, (U.S. Appl. No. 12/646,383), (dated Dec. 22, 2011),1-78.

Non-Final Office Action from PTO, (U.S. Appl. No. 13/558,380), (dated Oct. 4, 2012), 1-20.

Non-Final Office Action from PTO, (U.S. Appl. No. 12/646,603), (dated Oct. 13, 2011),1-74.

Non-Final Office Action from PTO, (U.S. Appl. No. 12/646,603), (dated Jun. 13, 2013), 1-16.

Non-Final Office Action from PTO, (U.S. Appl. No. 12/728,721), (dated Jan. 6, 2012), 1-31.

Non-Final Office Action from PTO, (U.S. Appl. No. 12/728,721), (dated May 9, 2013), 1-25.

Non-Final Office Action from PTO, (U.S. Appl. No. 12/815,037), (dated Mar. 28, 2012),1-17.

Non-Final Office Action from PTO, (U.S. Appl. No. 12/815,037), (dated Jul. 18, 2013), 1-19.

Non-Final Office Action from PTO, (U.S. Appl. No. 12/899,510), (dated Jan. 23, 2013), 1-20.

Non-Final Office Action from PTO, (U.S. Appl. No. 12/898,338), (dated Jun. 19, 2012), 1-16.

Non-Final Office Action from PTO, (U.S. Appl. No. 13/189,518), (dated Dec. 21, 2012), 1-10.

Non-Final Office Action from PTO, (U.S. Appl. No. 13/235,387), dated Sep. 12, 2013), 1-16.

PCT Search report and written opinion, (PCT/US2010/56935, (dated Jan. 12, 2011),1-9.

PCT Search report and written opinion, (PCT/US2011/35093, (dated Sep. 12, 2011),1-8.

PCT Search report and written opinion, (PCT/US11/54666), (dated Feb. 28, 2012), 1-13.

PCT Search report and written opinion, (PCT/US11/54668), dated Feb. 28, 2012, 1-12.

PCT Search report and written opinion, (PCT/US12/41785), (dated Aug. 17, 2012),1-10.

PCT Search report and written opinion, (PCT/US12/42843), (dated Aug. 31, 2012), 1-8.

PCT Search report and written opinion, (PCT/US2012/051554), (dated Oct. 19, 2012), 1-12.

PCT Search report and written opinion, (PCT/US12/59139), (dated Dec. 18, 2012), 1-15.

PCT Search report and written Opinion, (PCT/US13/20026), (dated Aug. 5, 2013), 1-14.

\* cited by examiner

METHOD AND APPARATUS FOR MONITORING MEDICATION ADHERENCE

CROSS REFERENCE TO RELATED APPLICATIONS

This application is a continuation of, and claims priority to, U.S. patent application Ser. No. 15/337,551 (now U.S. Pat. No. 9,844,337), Oct. 28, 2016, which is a continuation of, and claims priority to U.S. patent application Ser. No. 14/073,525 (now U.S. Pat. No. 9,486,720), filed Nov. 6, 2013, which is a continuation of, and claims priority to U.S. patent application Ser. No. 12/899,510 (now U.S. Pat. No. 8,605,165), filed Oct. 6, 2010. The contents of all of the prior applications are incorporated herein by reference in their entirety.

FIELD OF THE INVENTION

This invention relates generally to a method and apparatus for assisting monitoring of, and for improving medication adherence, and more particularly to an apparatus and method for providing feedback to a user of a gesture recognition system for monitoring of medication adherence related to positioning the user, a medication, or other object within an image acquisition area, and to provide positive feedback related to the position of the user, the medication and the like in order to encourage and improve adherence to medication administration protocols and to shape patient behavior in a positive manner. The invention may also act to insure and aid in the ability for proper acquisition of various gesture sequences and images when applied to an image acquisition system potentially having a narrow field of view, or a fixed direction camera. Failure on any of these fronts may result in additional instruction or encouragement from the system, in either an automated or personal manner, and may be provided as input data to an overall population management system.

BACKGROUND OF THE INVENTION

Gesture recognition systems typically include high sensitivity cameras including a wide field of view, multiple cameras, tracking systems, or any combination of the above. Such systems typically require custom system hardware systems to allow for proper image acquisition. When being employed to assist in monitoring medication adherence, it may not be possible or convenient to provide such a specialized device to each user.

Employing gesture recognition as well as object recognition and tracking to monitor medication adherence may result in the monitoring of individuals and medication. These individuals and the medication they are holding or administering may be improperly positioned within a field of view of the camera. While the higher quality gesture recognition systems noted above may be able to capture necessary images in spite of such variability, standard camera systems that may be provided in a standard computer or laptop configuration may not be sufficient for performing gesture recognition. Furthermore, mobile devices, typically including an even lower resolution camera and lower computing power may have more difficulty in implementing such a gesture recognition system.

Therefore, it would be desirable to provide an apparatus and system that allow for proper gesture recognition in such a context, even employing lower quality hardware components and processing power, and that overcomes other drawbacks of the prior art.

SUMMARY OF THE INVENTION

In accordance with various embodiments of the invention a gesture recognition assistance method and apparatus for assisting in monitoring medication adherence may be provided. Such an assistance method may include a directional system for insuring that a user is properly positioned within an image acquisition space. The directional system may preferably include a color and/or shape based indication system to direct a user to a location in an image acquisition space to insure proper image acquisition. Alternative embodiments of the invention may further include sound to aid in conveying information to a user. The directional system may also be employed to determine and instruct changes in location of a pill or other medication. In accordance with a preferred embodiment of the system, when implemented on a mobile device or other reduced processing power device, a user may attempt to have their image acquired by the device including a fixed, relatively low resolution camera, a user may be shown an image or other representation of themselves and including various indications of incorrect positioning. The user may further be shown various arrows indicating a direction in which to move. Further, color may be employed to give a further indication to the user of proper location.

Therefore, by providing such guidance to the user, not only is the user guided through a sequence of steps to aid in proper medication administration, by effectively reducing the variability in user behavior, the processing required to accurately determine whether the user is properly administering such medication is also reduced.

Furthermore, the present invention may also be applicable to additional forms of medication administration, such as injectables, inhalers, topical applications, ocular applications and the like, as well as various other medical maintenance procedures, such as user of cardiac monitors, or other monitoring devices or the like. Indeed, the invention may be applicable to any medical procedure in which reducing variability of patient behavior to allow for remote monitoring employing a gesture recognition system may be employed.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

Figure 12:
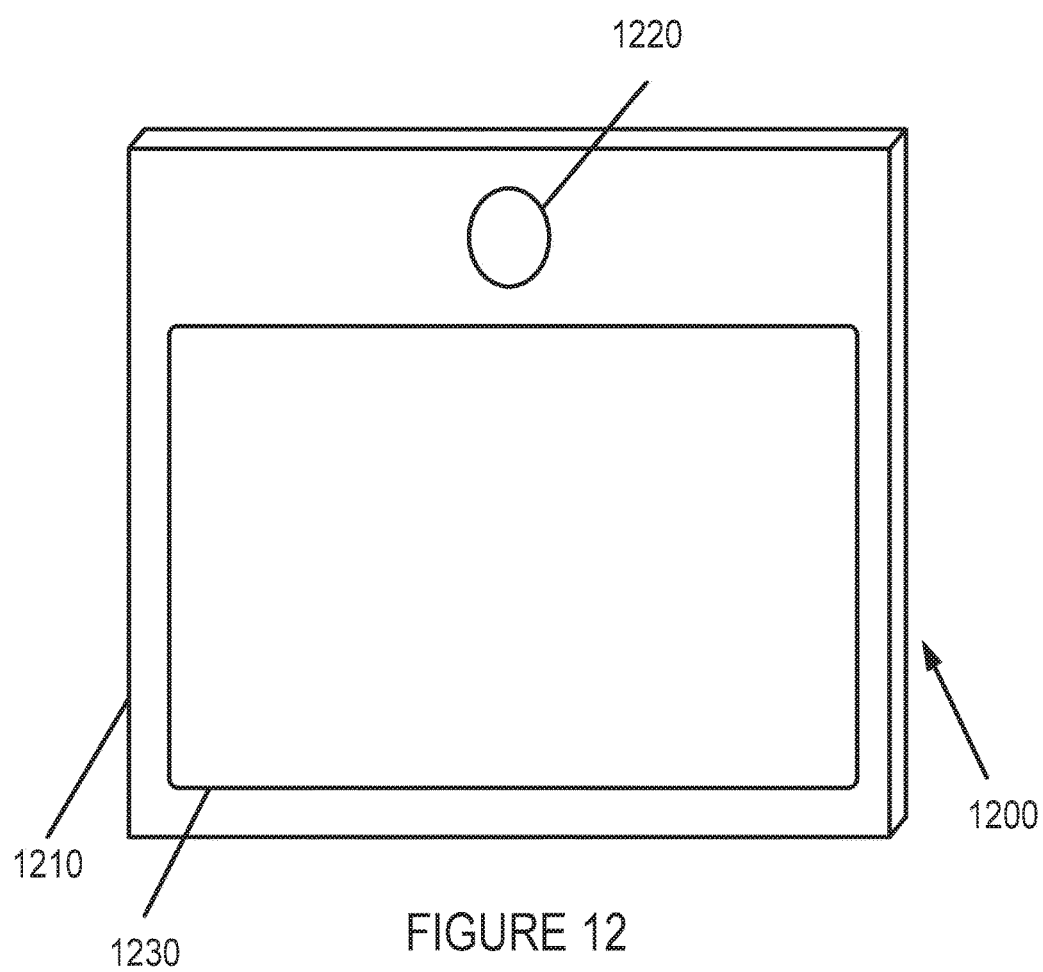
FIG. 12 depicts a display and image capture apparatus that may be employed in accordance with one or more embodiments of the present invention.

The invention will now be described making reference to the following drawings in which like reference numbers denote like structure or steps. Referring first to FIG. 12, a display and image capture apparatus 1200 that may be employed in accordance with one or more embodiments of the present invention is shown. Apparatus 1200 preferably includes a housing 1210, an image capture camera 1220 and a display 1230. Image capture camera 1220 may comprise a single camera element, a stereo camera element or other appropriate image capture device. Other elements, as known to one of ordinary skill in the art, including ports, power attachments, processors for processing data, and the like may also be provided in accordance with apparatus 1200. It is further contemplated in accordance with the various embodiments of the invention that apparatus may include one or more self-check mechanisms, including mechanisms for determining proper ambient light, direction and background of the camera and the background imaged by the camera, or other environmental issues that may be improved to further aid in the imaging of any images by apparatus 1200. Additionally, if at any time it is determined that lighting conditions are too difficult for imaging apparatus 1200, it may be possible to provide a light burst from a strobe or display to aid in illuminating the images to be captured. The following descriptions of the various embodiments of the invention will assume that such a display and image capture apparatus 1200 is employed. The invention, however, shall not be so limited and may be employed on any structure of image capture camera and display, whether contained in a single or multiple apparatuses.

Figure 1:
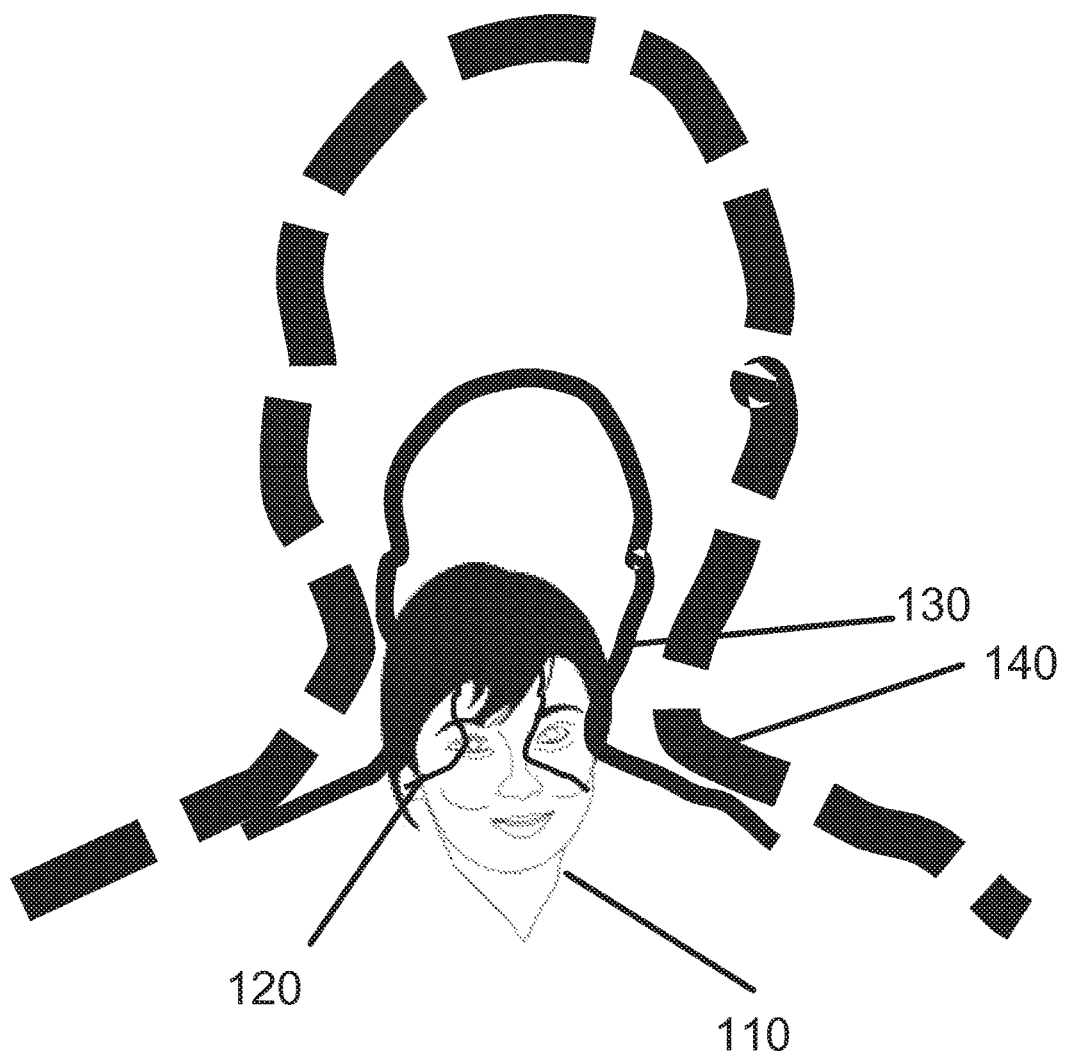
FIG. 1 depicts a user being directed to move closer to a display and image capture apparatus in accordance with an embodiment of the invention.

Referring next to FIG. 1, a face of a user 110 is shown on display 1230 of display and image capture apparatus 1200. As can be seen in FIG. 1, this face is shown as being small, an indication of being greater than a desired distance from an imaging apparatus. This situation of being too far away may be further accentuated by a small head tracing 120 being approximately the size of the user's head image. It has been determined by the inventors of the present invention that proper positioning of the face of a user improves the ability to perform various gesture recognition procedures, and in particular aids in reducing variability in action that must be processed by image capture apparatus 1200. Therefore, by reducing variability in position, and in turn therefore variability in action, gesture recognition for determining medication adherence may be performed in an easier manner. Furthermore, proper face positioning may be even more important when one considers reduced-resolution cameras. Thus, if the user is positioned too far, perhaps not enough pixels may be imaged to properly perform such gesture recognition, while being positioned too close may result in image capture device not being able to image the entire face of the user. Further, if lighting conditions are poor, the user may be asked to move closer to aid in image capture. Thus, proper positioning may also be provided as a method for addressing variations in camera resolution, processing power, lighting or other environmental conditions, and the like.

Figure 2:
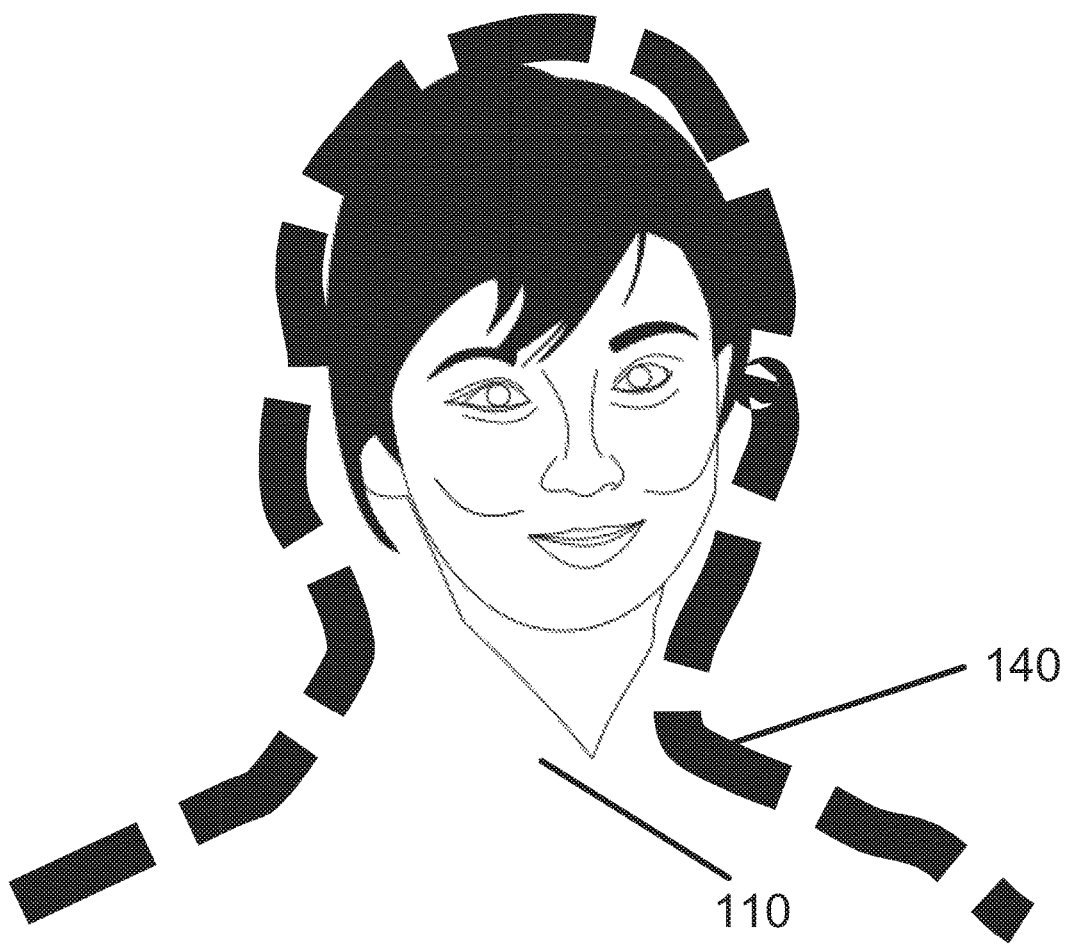
FIG. 2 depicts a user indicated as situated as being a proper distance from the display and image capture apparatus in accordance with an embodiment of the invention.

Also provided may be an intermediate sized head tracing 130 showing a direction in which the user is to move, and a full sized head tracing 140. Once the user's head is sized coincident with the full sized head tracing, it may be considered that the user is at a correct distance from the image capture camera and display, as is shown in FIG. 2. It is further contemplated that if the user is positioned closer than desired to image capture camera 1220, the user image may be shown on display 1230 as larger than the full sized head tracing 140. In either case, as is shown in FIG. 1, the desired sized head tracing 140 may be shown in a different line format than the other head tracings, in this exemplary case, a dotted line for the full sized head tracing 140, solid lines for the others. Of course any desired line formats may be used. Further, in addition to providing such head tracings, an avatar or other human or other indicator indicating a direction in which the user is to move may be provided on display 1230. Further, the incorrect head tracings may be provided in a first color, such as red, while the correct head tracing may be provided in a second color, such as green in order to further provide user feedback and an easy to recognize indication of correct or incorrect action. Any desirable combination of color and line format may be employed.

Figure 3:
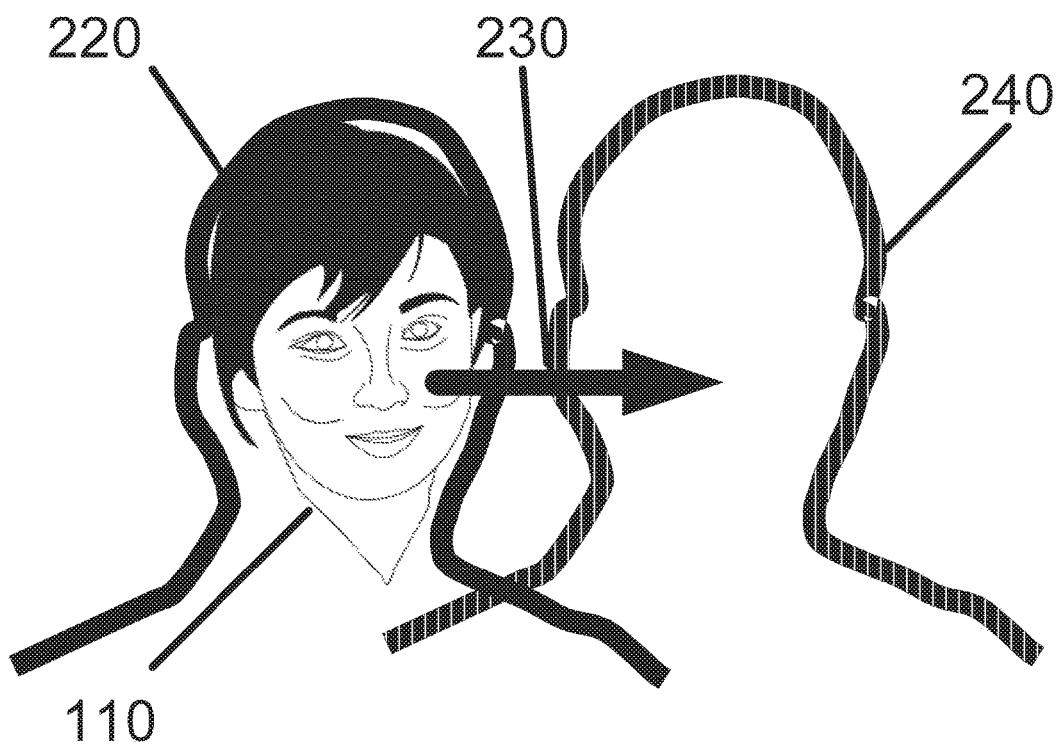
FIG. 3 depicts a user being directed to move laterally in relation to a display and image capture apparatus in accordance with an embodiment of the invention.

Referring next to FIG. 3, once a user is positioned a proper distance from display and image capture apparatus 1200 (or, alternatively, while the user is still not positioned a proper distance from the display and image capture apparatus 1200, the present embodiment being described for clarity), he or she may be positioned incorrectly in a lateral direction to a desired position. Thus as is shown, display 1230 may show an image of user 110 and may include a full sized head tracing 220 indicating a current position of the user (of course, the smaller and larger head tracings of FIG. 1 may be provided here if the user is also an incorrect distance from display and image capture apparatus 1200), and a desired position full head tracing 240. As shown, the head tracing and the desired head tracing are preferably drawn employing different line formats to indicate the desired position. An arrow 230 may also be provided indicating a direction in which the user is to move. As with FIG. 1, an avatar or other human or other indicator may also be provided on display 1230, indicating a direction in which the user is to move. Further, the incorrect head tracings may be provided in a first color, such as red, while the correct head tracing may be provided in a second color, such as green. In addition, the same red or other color may be used to illuminate a side of the image if the user moves off the screen in a particular direction, the side of movement being illuminated on display 1230.

Figure 4:
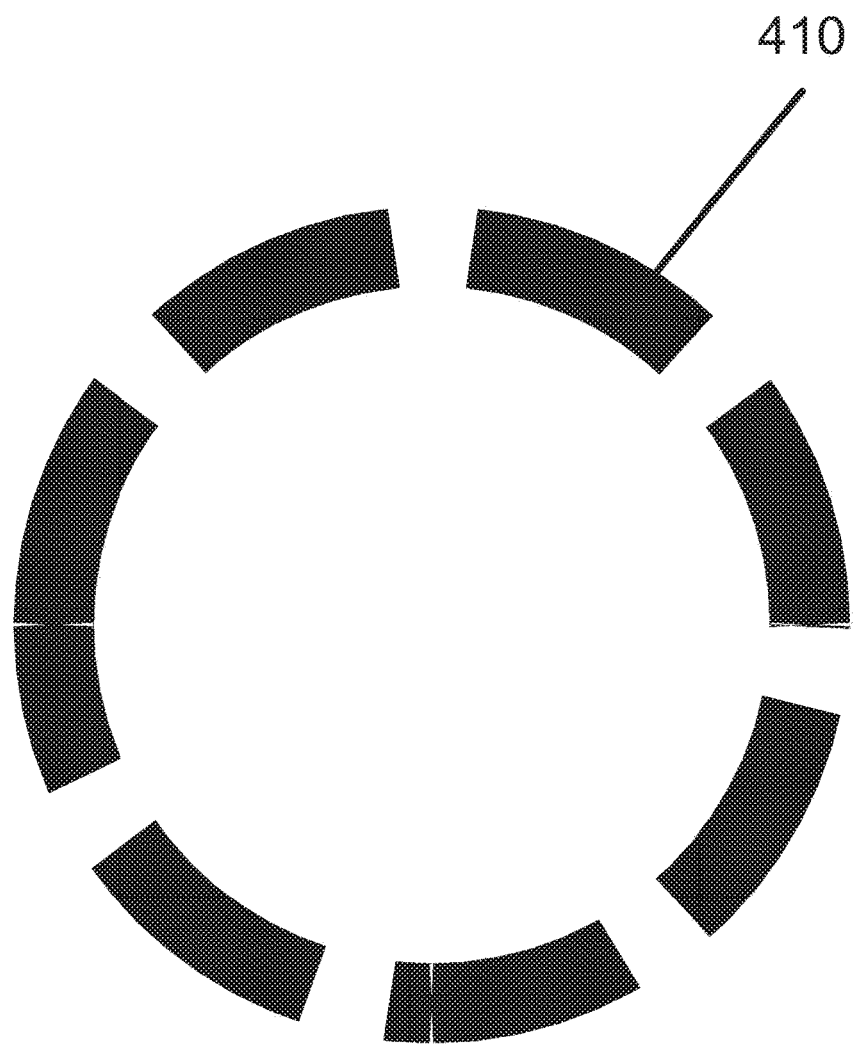
FIG. 4 depicts a position target in accordance with an embodiment of the invention.
Figure 5:
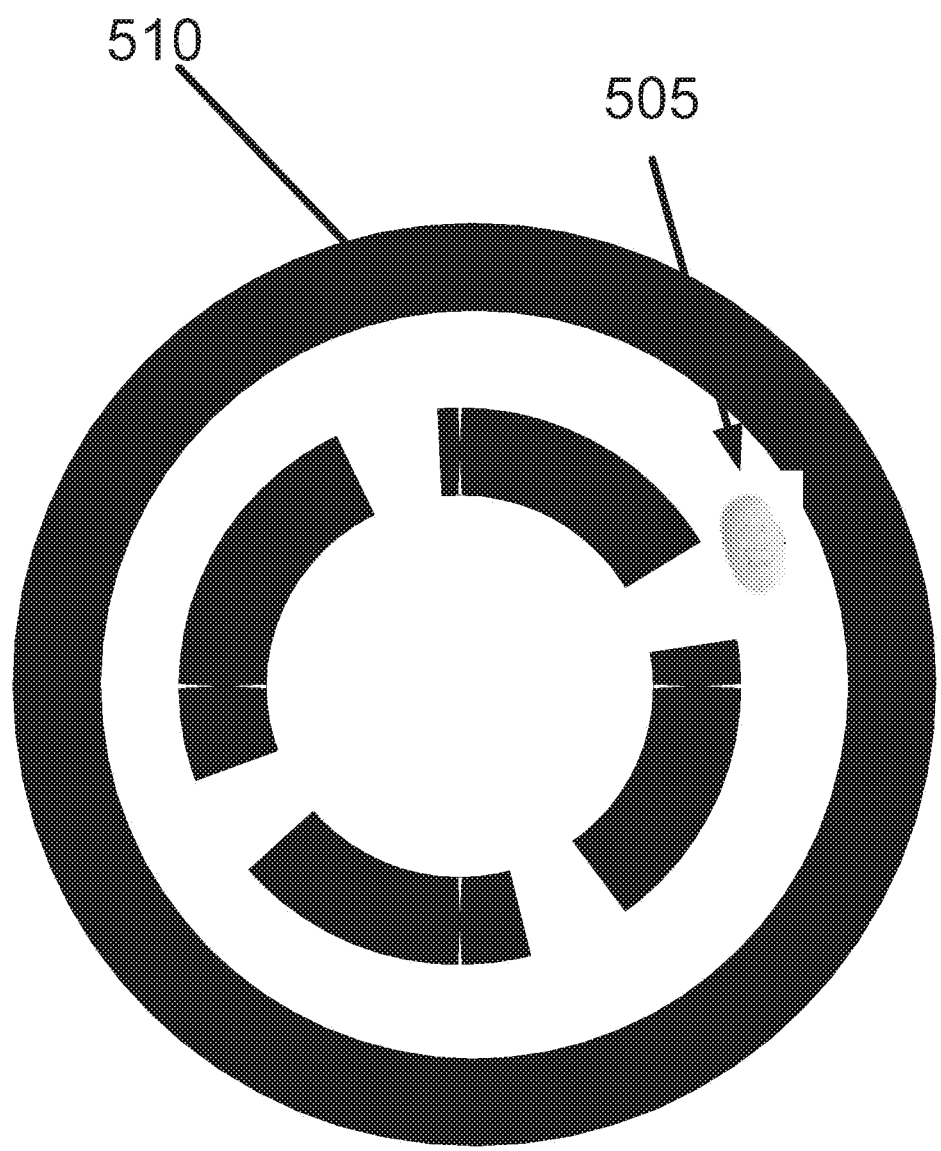
FIG. 5 depicts a position indicator in accordance with an embodiment of the invention.
Figure 6:
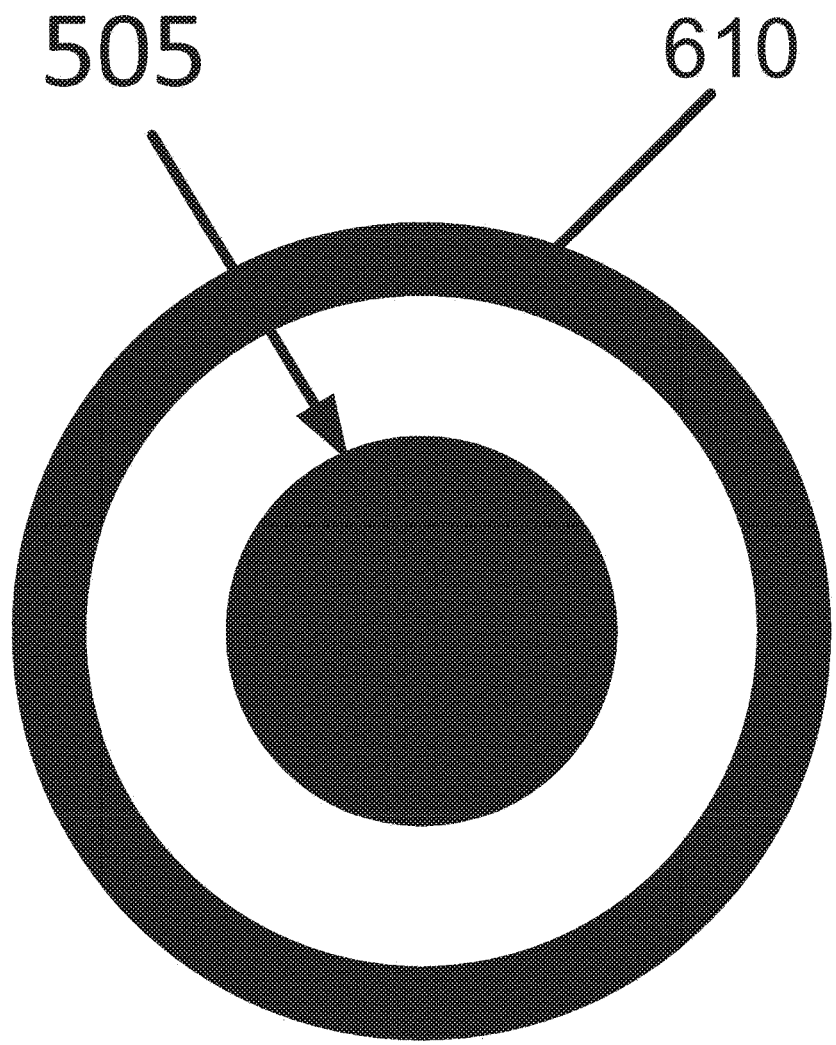
FIG. 6 depicts a position indicator indicating that a desired object has been identified in accordance with an embodiment of the invention.
Figure 7:
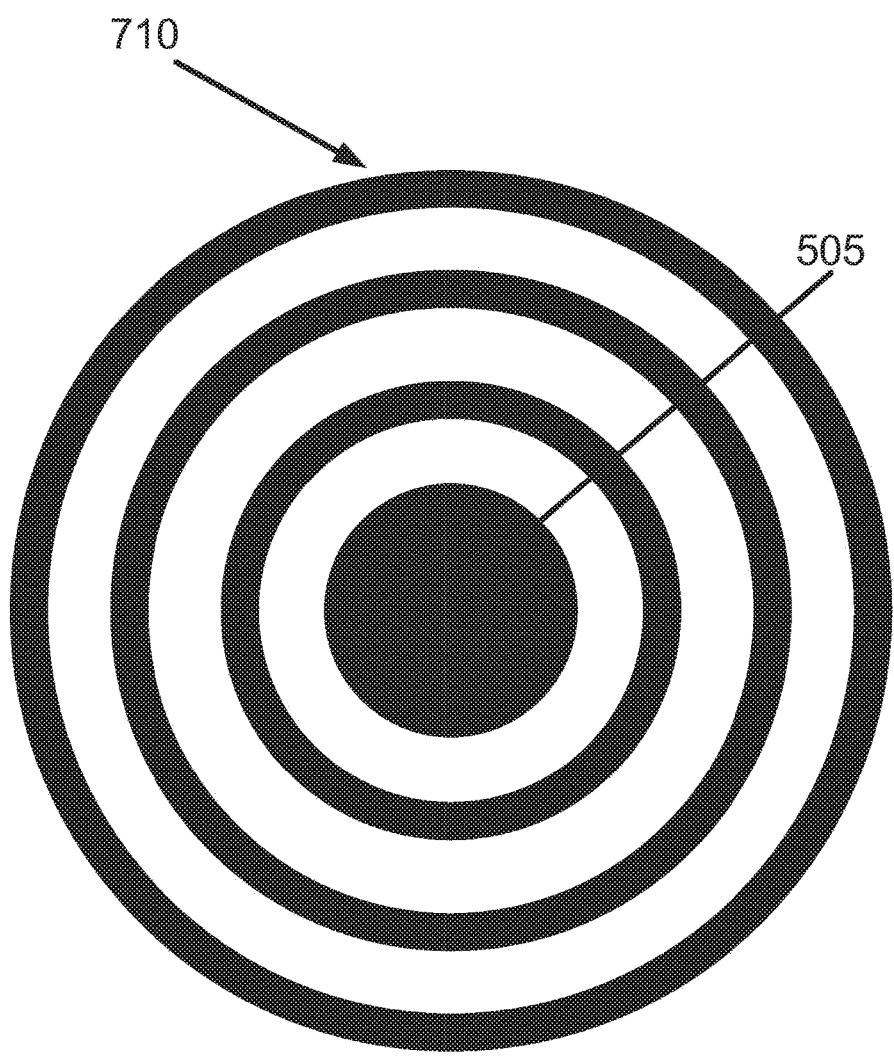
FIG. 7 depicts a position indicator and target indicating that the position indicator has reached the desired target to provide positive reinforcement to a user in accordance with an embodiment of the invention.

Next, FIGS. 4-7 depict an embodiment of the invention for locating a single or group of objects, and in accordance with this embodiment of the invention such an object may comprise a pill or other medication to be ingested by a user. Thus, as is shown in FIG. 4, a circular indicator 410 may be provided on display 1230 indicative of a first position that the user is to place the object or in this situation, a pill. Of course, for this circular indicator and any other indicators described in accordance with the invention, any desired indicators may be employed. The invention may be similarly applicable to other medication administration procedures, employing for example, injectables, inhalers, topical applications, ocular applications and the like, as well as various other medical maintenance procedures, such as user of cardiac monitors, or other monitoring devices or the like, or any other medical device that may benefit from remote, automated monitoring. As is then shown in FIG. 5, a pill 505 is shown adjacent indicator 410, as is shown by the outer ring proximity indicator 510. Once the pill is positioned concentric with the indicator 410 and the proximity indicator, the pill is shown in a target bulls eye 610, including an outer ring and a center indicator. To properly position pill 505, target bulls eye 610 as the user moves pill 505, target bulls eye moves in display 1230 in a similar manner. Thus, movement in both the lateral direction and in the direction towards and away from image capture apparatus 1200 may be monitored, and feedback provided to the user. For example, as the user moves pill 505 closer to display 1230, the pill and indicator 410 may grow larger, while movement away from the display may cause the indicator to shrink. Thus, in addition to assisting the user in placing the pill properly laterally, the indicator system may also aid in positioning the pill a proper distance from the image capture apparatus 1200. Concentric larger rings 710 (as shown in FIG. 7) may be positioned on display 1230 to indicate a desired position to which the user is to move pill 505. When the target bulls eye is positions concentric to larger rings 710, and is indicated as being a correct size to fit therein, thus providing a concentric set of circles on display 1230, it can be determined by the user that pill 505 has been properly positioned in the various desired directions. As with the earlier embodiments, arrows or other directional indicators may be provided, and color may be used to aid in directing the user. Thus, a red color may be used to indicate a side of an image to which the pill may have been moved off the screen.

Figure 8:
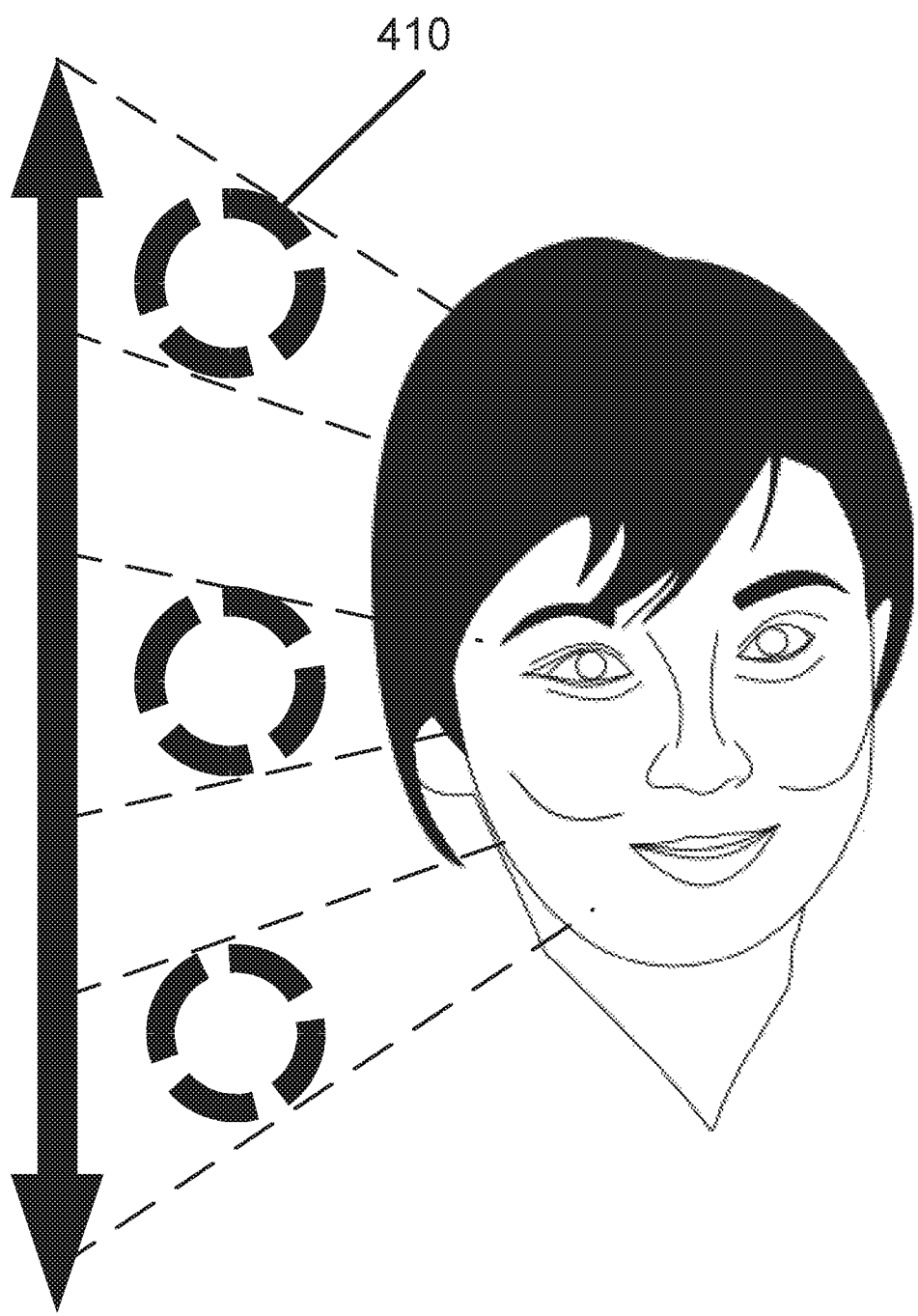
FIG. 8 depicts various positioning locations of a position indicator in relation to the display and image acquisition apparatus to provide an indication of position relative to the camera and mouth of the user in accordance with an embodiment of the invention.

Referring next to FIG. 8, if a user is positioning a pill, or is to position a pill on the display, indicator 410 may be shown on display 1230 in various locations vertically in order to account for relative vertical positioning of the image acquisition camera relative to the user. Thus, if the camera is positioned above the user, the user will be encouraged to hold the pill at a higher location, thus allowing for the imaging of the pill and user at the same time. Similarly, if the camera is positioned lower than the user, the user will be encouraged to hold the pill at a lower location, thus being positioned approximately between the camera and the user's face, as shown by the lower indicator 410 in FIG. 8. Thus, indicator 410 may be positioned in any location along the arrow shown in FIG. 8 to ensure proper pill location to aid in proper imaging of the user and the pill. Such positioning further aids in reducing the possibility of occlusion of the pill or other medication by the hand of the user, or other possible occlusion, and additionally aids in keeping the pill or other medication within the field of view of image capture camera 1220.

Figure 9:
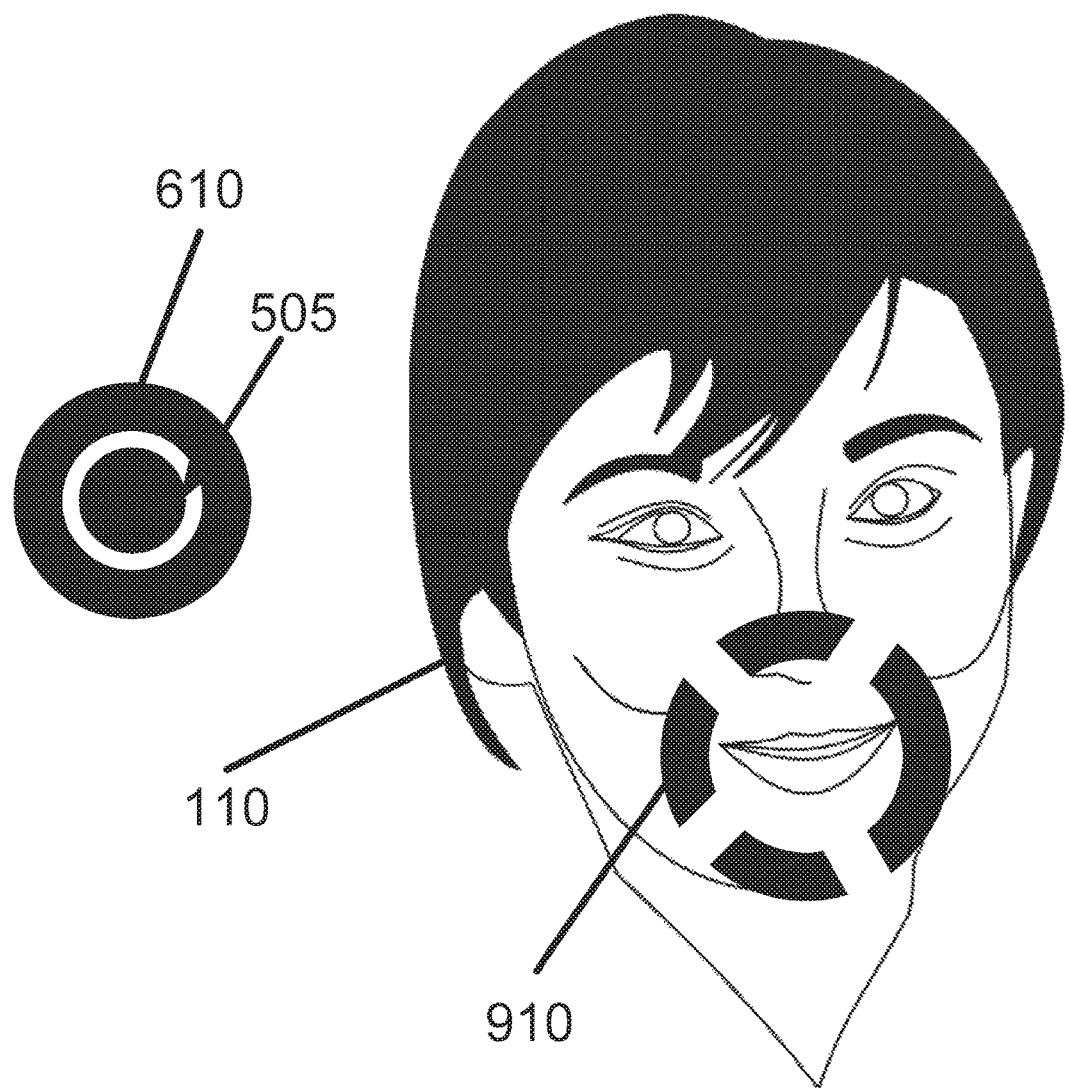
FIG. 9 depicts a position indicator indicating that a desired object has been identified in relation to a mouth position indicator target in accordance with an embodiment of the invention.
Figure 10:
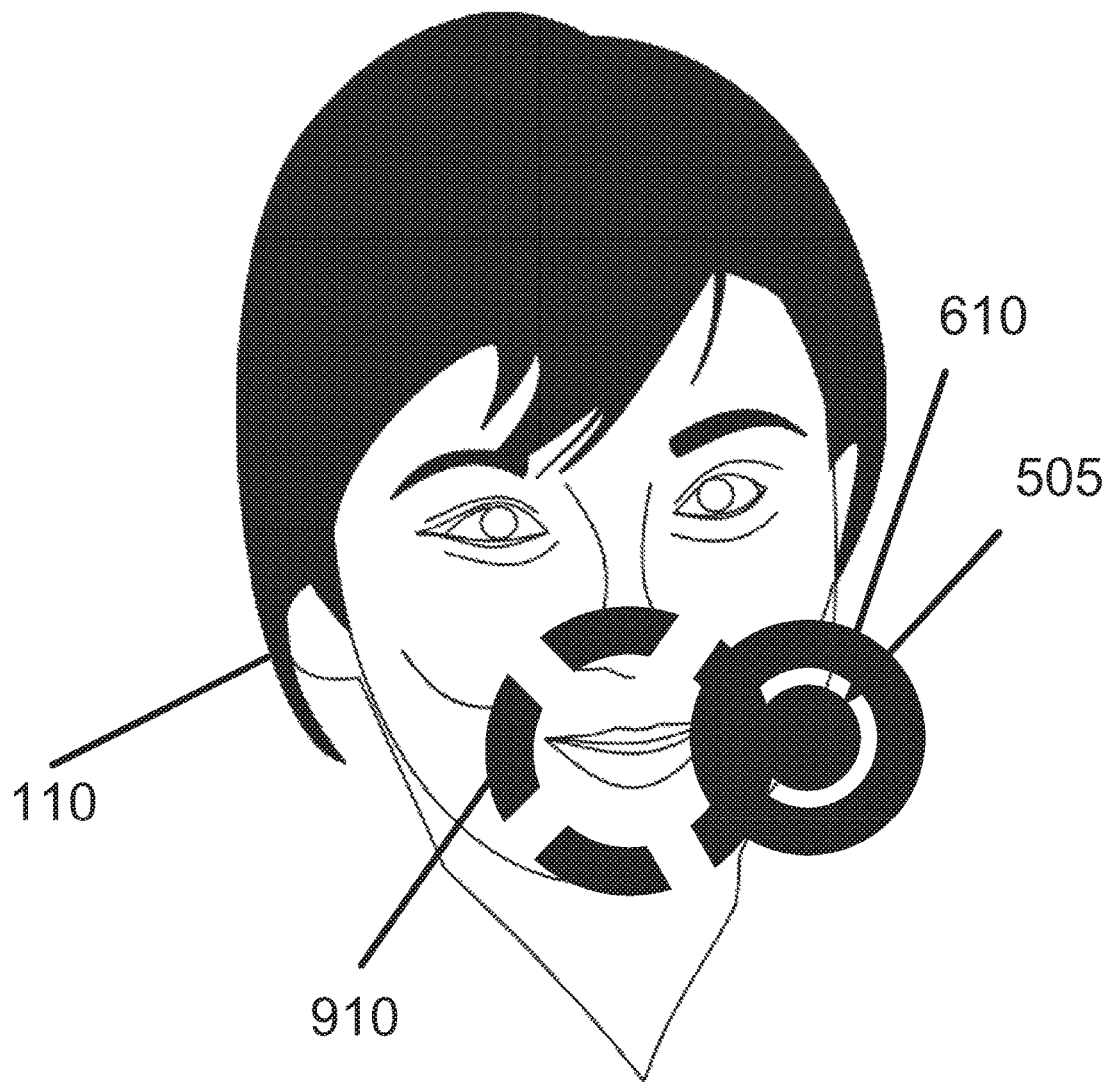
FIG. 10 depicts the position indicator of FIG. 9 in a different position relative to the mouth position indicator target of FIG. 9 in accordance with an embodiment of the invention.

Referring next to FIG. 9, a method and system for aiding in confirming pill ingestion by a user in accordance with an embodiment of the invention is shown. Once again, a pill 505 is included under a target bulls eye 610 as originally portrayed in FIG. 6. Also shown in a location target 910, similar to the concentric large rings 710 of FIG. 7. Location target 910, however, is preferably provided to determine and indicate a location of the user's mouth on display 1230. Therefore, in accordance with the invention, the user's mouth location is determined in accordance with the image acquisition camera, and thereafter, location target 910 may be provided on display 1230 coincident therewith. As is further shown in FIG. 10, as the user moves pill 505, target bulls eye 610 follows along, indicating a relative position as compared with location target 910 on display 1230. Various techniques noted above, including arrows, color and the like may be employed in aiding the user in positioning pill 505 concentric with location target 910. Of course, as the position of location target 910 is preferably coextensive with the user's mouth, movement of the pill to the user's mouth may result in the desired interaction between pill 505 and location target 910, thus encouraging the desired action. It is through this continual monitoring that the user is further encouraged to want to perform actions correctly. As if being watched, the automated system provided in accordance with various embodiments of the present invention provides positive reinforcement to a user, and also may provided the added incentive of consistent and continuous monitoring. Rather than requiring an actual person to continuously review the actions of the user, automatic monitoring and feedback may provide a similar user response without the need for additional personnel. Furthermore, such an automated system may provide even greater consistency in monitoring, thus further encouraging desired behavior and further reducing variability in user action.

Figure 11:
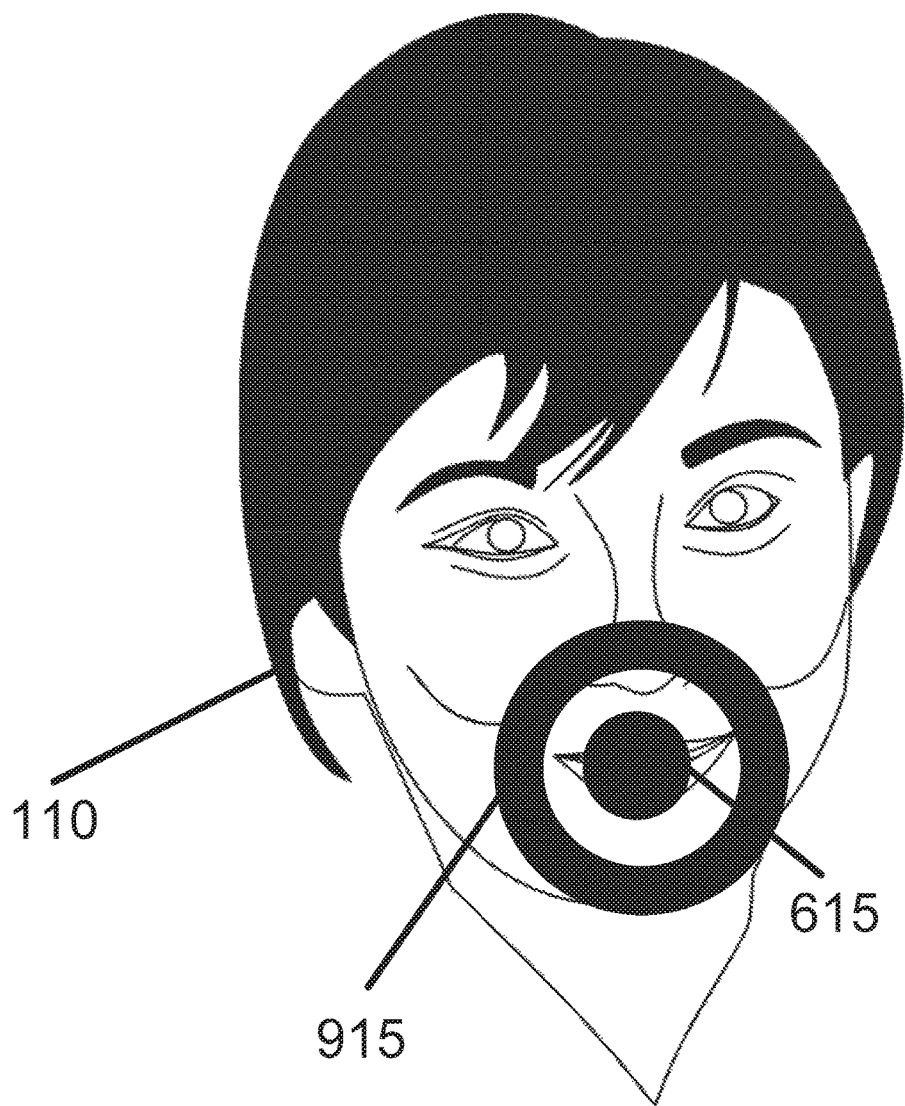
FIG. 11 depicts the position indicator of FIG. 9 and the mouth position indicator of FIG. 9 indicating that the position indicator has reached the desired mouth position indicator target position in accordance with an embodiment of the invention.

Once properly positioned, as is shown in FIG. 11, properly positioned locator 615 is shown in a differently displayed location target 915, thus indicating successful positioning. As noted above, color change, change in line texture or the like may be used to indicate that the user has properly positioned the pill relative to their mouth, thus providing positive feedback to the user upon proper action having been taken.

Therefore, in accordance with the invention, a set of one or more indicators may be provided to a user to aid in proper following of a predetermined script to aid in the proper acquisition of the various movements of the user, so that the system is able to determine whether the user is properly positioned in front of an image acquisition camera, and whether the user has properly positioned a pill for ingestion. Various positive reinforcement mechanisms may be employed in accordance with the monitoring system of the various embodiments of the invention, thus encouraging the user to properly perform various actions and reducing the variability in such actions, therefore easing the burden on the system to properly determine proper performance of such actions by the user. The user may also perceive the system as one that is easy to use, thus even further encouraging its use.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A method for positioning a user in a field of view of an image acquisition camera by providing automatic guidance to the user on how to position the user, the method comprising the steps of:
   displaying on a display an image of a user within a field of view of an image acquisition camera;
   determining a desired location of a user in a field of view of an image acquisition camera;
   determining a current position of the user in the field of view of the image acquisition apparatus;
   presenting a location target on the display indicating a movement to be made by the user to move the current position of the user towards the desired location of the user in the field of view of the image acquisition camera;
   acquiring an image of the user within the field of view of the image acquisition camera by the image acquisition camera;
   following movement of the user in the field of view of the image acquisition camera by relative movement of the user image on the display; and
   confirming interaction between the user and the location target when they are determined to be coextensive on the display.

2. The method of claim 1, wherein if the current position of the user is too far from the image acquisition camera, an image of the user is displayed on the display in a small size.

3. The method of claim 2, further comprising the step of providing a head tracing indicating a proper size that the image of the user should be.

4. The method of claim 3, wherein an indicator is provided when the user is properly positioned, and the image of the user is coincident with the head tracing.

5. The method of claim 4, wherein the step of indicating comprises a change in color.

6. The method of claim 1, wherein the desired location of the user is adjusted in accordance with one or more environmental factors.

7. The method of claim 1, wherein the display further displays an indication if the user moves out of the field of view of the image acquisition camera and is therefore no longer displayed on the display.

8. The method of claim 1, further comprising the step of providing a head tracing indicating a desired proper location of the image of the user.

9. The method of claim 8, wherein an indicator directs the user to move in the direction of the head tracing.

10. A system for tracking positioning of a user by providing automatic guidance to the user on how to position the user, comprising:
    a display for displaying an image of a user within a field of view of an image acquisition camera
    an image acquisition apparatus for acquiring an image of a user;
    a processor for determining a desired location of a body part of a user in a field of view of the image acquisition apparatus, and determining a current position of the body part of the user in the field of view of the image acquisition apparatus; and
    a display for displaying the acquired image of the user, for presenting a location target indicating a movement to be made by the user to move the body part of the user to a desired location within the field of view of the image acquisition camera;
    the processor further following movement of the user in the field of view of the image acquisition camera by relative movement of the user image on the display, confirming interaction between the user and the location target when they are determined to be coextensive on the display.

11. The system of claim 10, wherein the display further displays a first indicator of the desired location of the body part of the user within the field of view of the image acquisition camera and a second indicator of the current position of body part of the user within the field of view of the image acquisition camera.

12. The system of claim 11, wherein the indicated movement is indicative of moving the second indicator towards the first indicator within the field of view of the image acquisition camera.

13. The system of claim 12, wherein provision of the indicated movement improves the ability of the user to properly position their body part within the field of view of the image acquisition camera.

14. The system of claim 11, wherein positioning of the body part of the user is confirmed when the first indicator and the second indicator are determined to be coextensive in one or more of the plurality of images.

15. The system of claim 10, wherein the display further displays an indication if body part moves out of the field of view of the image acquisition camera.

* * * * *

UNITED STATES PATENT AND TRADEMARK OFFICE
CERTIFICATE OF CORRECTION

PATENT NO.       : 10,149,648 B2
APPLICATION NO.  : 15/840836
DATED            : December 11, 2018
INVENTOR(S)      : Adam Hanina, Gordon Kessler and Lei Guan Page 1 of 1

It is certified that error appears in the above-identified patent and that said Letters Patent is hereby corrected as shown below:

In the Specification

Column 1, Line 9:
After "9,844,337)," insert -- filed --, therefor.

In the Claims

Column 7, Line 51, in Claim 5:
Delete "step of indicating" and insert -- indicator --, therefor.

Column 8, Line 3, in Claim 8:
Delete "1," and insert -- 7, --, therefor.

Column 8, Line 6, in Claim 9:
Delete "an" and insert -- the --, therefor.

Column 8, Line 55, in Claim 15:
Delete "if body" and insert -- if the body --, therefor.

Signed and Sealed this
Ninth Day of July, 2019

Andrei Iancu
*Director of the United States Patent and Trademark Office*